US011285171B2

(12) United States Patent
Qhattal

(10) Patent No.: US 11,285,171 B2
(45) Date of Patent: *Mar. 29, 2022

(54) NITRIC OXIDE RELEASING SUPPOSITORIES AND METHODS OF USE THEREOF

(71) Applicant: Novan, Inc., Morrisville, NC (US)

(72) Inventor: Hussaini Syed Sha Qhattal, Morrisville, NC (US)

(73) Assignee: Novan, Inc., Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/975,843

(22) PCT Filed: Mar. 1, 2019

(86) PCT No.: PCT/US2019/020209
§ 371 (c)(1),
(2) Date: Aug. 26, 2020

(87) PCT Pub. No.: WO2019/169221
PCT Pub. Date: Sep. 6, 2019

(65) Prior Publication Data
US 2020/0397815 A1 Dec. 24, 2020

Related U.S. Application Data

(60) Provisional application No. 62/637,120, filed on Mar. 1, 2018.

(51) Int. Cl.
| | | |
|---|---|---|
| *A61K 9/02* | (2006.01) | |
| *A61K 47/44* | (2017.01) | |
| *C01B 21/24* | (2006.01) | |
| *A61K 33/00* | (2006.01) | |
| *A61K 9/00* | (2006.01) | |
| *A61K 47/10* | (2017.01) | |
| *A61K 47/12* | (2006.01) | |
| *A61K 47/24* | (2006.01) | |
| *A61K 47/42* | (2017.01) | |
| *C01B 21/40* | (2006.01) | |

(52) U.S. Cl.
CPC ............ *A61K 33/00* (2013.01); *A61K 9/0036* (2013.01); *A61K 47/10* (2013.01); *A61K 47/12* (2013.01); *A61K 47/24* (2013.01); *A61K 47/42* (2013.01); *A61K 47/44* (2013.01)

(58) Field of Classification Search
CPC .... A61K 2300/00; A61K 31/80; A61K 33/00; A61K 47/02; A61K 47/10; A61K 47/12; A61K 47/24; A61K 47/42; A61K 47/44; A61K 9/0034; A61K 9/0036; A61K 9/02; A61L 2300/114; A61M 2202/0275

See application file for complete search history.

(56) References Cited

U.S. PATENT DOCUMENTS

| | | |
|---|---|---|
| 4,917,866 A | 4/1990 | Abe et al. |
| 5,968,528 A | 10/1999 | Deckner et al. |
| 6,103,266 A | 8/2000 | Tapolsky et al. |
| 6,319,913 B1 | 11/2001 | Mak et al. |
| 6,479,058 B1 | 11/2002 | McCadden |
| 7,704,518 B2 | 4/2010 | Tamarkin et al. |
| 8,241,650 B2 | 8/2012 | Peters |
| 8,282,967 B2 | 10/2012 | Schoenfisch et al. |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,591,876 B2 | 11/2013 | Bauman et al. |
| 8,617,100 B2 | 12/2013 | Eini et al. |
| 8,636,982 B2 | 1/2014 | Tamarkin et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 8,937,143 B2 | 1/2015 | Bao et al. |
| 8,956,658 B2 | 2/2015 | Schoenfisch et al. |
| 8,962,029 B2 | 2/2015 | Schoenfisch et al. |
| 8,981,139 B2 | 3/2015 | Schoenfisch et al. |
| 9,101,662 B2 | 8/2015 | Tamarkin et al. |
| 9,161,916 B2 | 10/2015 | Tamarkin et al. |
| 9,187,501 B2 | 11/2015 | Schoenfisch et al. |
| 9,238,038 B2 | 1/2016 | Schoenfisch et al. |

(Continued)

FOREIGN PATENT DOCUMENTS

| | | |
|---|---|---|
| CN | 101732728 A | 6/2010 |
| CN | 101791411 A | 8/2010 |

(Continued)

OTHER PUBLICATIONS

Utoguchi et al. (Pharmaceutical Research 1998;15(6):870-876) (Year: 1998).*

(Continued)

*Primary Examiner* — Ernst V Arnold
(74) *Attorney, Agent, or Firm* — Myers Bigel, P.A.

(57) ABSTRACT

The present invention relates generally to suppositories that release nitric oxide, and methods of using the same. According to some embodiments of the present invention provided herein is a nitric oxide (NO) releasing suppository (e.g., vaginal suppositories) are described herein. Some embodiments are directed to compositions, kits, and/or methods for treating and/or preventing an infection (e.g., a viral infection). In some embodiments, a method of treating and/or preventing a viral infection in a subject in need thereof is provided.

24 Claims, No Drawings

(56) References Cited

U.S. PATENT DOCUMENTS

| | | | |
|---|---|---|---|
| 9,265,725 B2 | 2/2016 | Tamarkin et al. | |
| 9,289,442 B2 | 3/2016 | Doxey et al. | |
| 9,320,705 B2 | 4/2016 | Tamarkin et al. | |
| 9,381,381 B2 | 7/2016 | Benjamin | |
| 9,427,605 B2 | 8/2016 | Peters | |
| 9,669,041 B2 | 6/2017 | Stasko et al. | |
| 9,757,397 B2 | 9/2017 | Kougoulos et al. | |
| 9,855,211 B2 | 1/2018 | Doxey et al. | |
| 10,206,947 B2 | 2/2019 | Doxey et al. | |
| 10,258,564 B2 | 4/2019 | Doxey et al. | |
| 10,322,081 B2 | 6/2019 | McHale et al. | |
| 2002/0013304 A1 | 1/2002 | Wilson et al. | |
| 2002/0028223 A1 | 3/2002 | Vatter et al. | |
| 2002/0165122 A1 | 11/2002 | Heaton et al. | |
| 2005/0038473 A1 | 2/2005 | Tamarkin et al. | |
| 2005/0232869 A1 | 10/2005 | Tamarkin et al. | |
| 2005/0271596 A1 | 12/2005 | Friedman et al. | |
| 2006/0160897 A1 | 7/2006 | Pelicci et al. | |
| 2006/0269620 A1 | 11/2006 | Morris et al. | |
| 2006/0275218 A1 | 12/2006 | Tamarkin et al. | |
| 2007/0166255 A1 | 7/2007 | Gupta | |
| 2007/0292359 A1 | 12/2007 | Friedman et al. | |
| 2007/0292461 A1 | 12/2007 | Tamarkin et al. | |
| 2008/0031907 A1 | 2/2008 | Tamarkin et al. | |
| 2008/0044444 A1 | 2/2008 | Tamarkin et al. | |
| 2008/0063607 A1 | 3/2008 | Tamarkin et al. | |
| 2008/0069779 A1 | 3/2008 | Tamarkin et al. | |
| 2008/0071206 A1 | 3/2008 | Peters | |
| 2008/0138296 A1 | 6/2008 | Tamarkin et al. | |
| 2008/0152596 A1 | 6/2008 | Friedman et al. | |
| 2008/0166303 A1 | 7/2008 | Tamarkin et al. | |
| 2008/0206155 A1 | 8/2008 | Tamarkin et al. | |
| 2008/0206159 A1 | 8/2008 | Tamarkin et al. | |
| 2008/0206161 A1 | 8/2008 | Tamarkin et al. | |
| 2008/0253973 A1 | 10/2008 | Tamarkin et al. | |
| 2008/0260655 A1 | 10/2008 | Tamarkin et al. | |
| 2008/0292560 A1 | 11/2008 | Tamarkin et al. | |
| 2008/0311163 A1 | 12/2008 | Peters | |
| 2008/0317679 A1 | 12/2008 | Tamarkin et al. | |
| 2009/0041680 A1 | 2/2009 | Tamarkin et al. | |
| 2009/0068118 A1 | 3/2009 | Eini et al. | |
| 2009/0130029 A1 | 5/2009 | Tamarkin et al. | |
| 2009/0175799 A1 | 7/2009 | Tamarkin et al. | |
| 2009/0214618 A1* | 8/2009 | Schoenfisch | A61P 37/02 424/426 |
| 2009/0297634 A1 | 12/2009 | Friedman et al. | |
| 2010/0098733 A1 | 4/2010 | Stasko | |
| 2010/0221195 A1 | 9/2010 | Tamarkin et al. | |
| 2010/0239512 A1 | 9/2010 | Morris et al. | |
| 2010/0266510 A1 | 10/2010 | Tamarkin et al. | |
| 2010/0286285 A1 | 11/2010 | Barthez et al. | |
| 2010/0310476 A1 | 12/2010 | Tamarkin et al. | |
| 2010/0331968 A1 | 12/2010 | Morris et al. | |
| 2011/0045037 A1 | 2/2011 | Tamarkin et al. | |
| 2011/0052650 A1 | 3/2011 | Morris et al. | |
| 2011/0086234 A1 | 4/2011 | Stasko et al. | |
| 2011/0097279 A1 | 4/2011 | Tamarkin et al. | |
| 2011/0195935 A1 | 8/2011 | Farber | |
| 2011/0212033 A1 | 9/2011 | Tamarkin et al. | |
| 2012/0134951 A1 | 5/2012 | Stasko et al. | |
| 2012/0136323 A1 | 5/2012 | Stasko et al. | |
| 2012/0141384 A1 | 6/2012 | Tamarkin | |
| 2012/0237453 A1 | 9/2012 | Tamarkin et al. | |
| 2013/0164225 A1 | 6/2013 | Tamarkin et al. | |
| 2013/0189191 A1 | 7/2013 | Tamarkin et al. | |
| 2013/0189193 A1 | 7/2013 | Tamarkin et al. | |
| 2013/0189195 A1 | 7/2013 | Tamarkin et al. | |
| 2013/0310533 A1 | 11/2013 | Bao et al. | |
| 2013/0344334 A1 | 12/2013 | Schoenfisch et al. | |
| 2014/0134321 A1 | 5/2014 | Stasko et al. | |
| 2014/0193502 A1 | 7/2014 | Tamarkin et al. | |
| 2014/0248219 A1 | 9/2014 | Tamarkin et al. | |
| 2014/0271494 A1 | 9/2014 | Tamarkin et al. | |
| 2014/0369949 A1 | 12/2014 | Peters | |
| 2015/0017103 A1 | 1/2015 | Tamarkin et al. | |
| 2015/0024052 A1 | 1/2015 | Doxey | |
| 2015/0025060 A1 | 1/2015 | Tamarkin et al. | |
| 2015/0111973 A1 | 4/2015 | Bauman et al. | |
| 2015/0118164 A1 | 4/2015 | Tamarkin et al. | |
| 2016/0030569 A1* | 2/2016 | Friend | A61K 9/06 514/81 |
| 2016/0106657 A9 | 4/2016 | Peters | |
| 2016/0199295 A1 | 7/2016 | Doxey et al. | |
| 2017/0196905 A1 | 7/2017 | Doxey et al. | |
| 2018/0200541 A1 | 7/2018 | Doxey et al. | |
| 2018/0008533 A1 | 11/2018 | McHale et al. | |
| 2018/0319822 A1 | 11/2018 | Schoenfisch et al. | |

FOREIGN PATENT DOCUMENTS

| | | | |
|---|---|---|---|
| EP | 1707224 A1 | 10/2006 | |
| EP | 1861130 B1 | 9/2008 | |
| EP | 1871433 B1 | 4/2009 | |
| EP | 1846058 B1 | 7/2009 | |
| EP | 2119459 A1 | 11/2009 | |
| EP | 2142179 A1 | 1/2010 | |
| EP | 2142181 A1 | 1/2010 | |
| EP | 1917005 B1 | 9/2010 | |
| JP | H0344396 U | 4/1991 | |
| JP | 07145053 A * | 6/1995 | |
| JP | 2003212773 A | 7/2003 | |
| WO | 9944622 A1 | 9/1999 | |
| WO | 0121148 A1 | 3/2001 | |
| WO | 03095398 A2 | 11/2003 | |
| WO | 2005004984 A1 | 1/2005 | |
| WO | 2006084910 A2 | 8/2006 | |
| WO | 2006084912 A1 | 8/2006 | |
| WO | 2006100154 A1 | 9/2006 | |
| WO | 2007007208 A2 | 1/2007 | |
| WO | 2007023005 A1 | 3/2007 | |
| WO | 2007023396 A2 | 3/2007 | |
| WO | 2007054818 A2 | 5/2007 | |
| WO | 2008032212 A2 | 3/2008 | |
| WO | 2008038140 A2 | 4/2008 | |
| WO | 2008038147 A2 | 4/2008 | |
| WO | 2008094866 A1 | 8/2008 | |
| WO | 2008110872 A2 | 9/2008 | |
| WO | 2008116497 A1 | 10/2008 | |
| WO | 2008116925 A1 | 10/2008 | |
| WO | 2008152444 A2 | 12/2008 | |
| WO | 2009007785 A2 | 1/2009 | |
| WO | 2009049208 A1 | 4/2009 | |
| WO | 2009056991 A2 | 5/2009 | |
| WO | 2009072007 A2 | 6/2009 | |
| WO | 2009087578 A2 | 7/2009 | |
| WO | 2009090495 A2 | 7/2009 | |
| WO | 2009098595 A2 | 8/2009 | |
| WO | 2009131931 A1 | 10/2009 | |
| WO | 2010016686 A2 | 2/2010 | |
| WO | 2010044875 A2 | 4/2010 | |
| WO | 2011005846 A1 | 1/2011 | |
| WO | 2011022652 A1 | 2/2011 | |
| WO | 2011022680 A2 | 2/2011 | |
| WO | 2011047013 A1 | 4/2011 | |
| WO | 2011061519 A2 | 5/2011 | |
| WO | 2011085484 A1 | 7/2011 | |
| WO | 2012001403 A1 | 1/2012 | |
| WO | 2012035468 A2 | 3/2012 | |
| WO | WO-2012041966 A1 * | 4/2012 | A61K 9/0034 |
| WO | 2012082976 A1 | 6/2012 | |
| WO | 2012100174 A1 | 7/2012 | |
| WO | 2012118819 A2 | 9/2012 | |
| WO | 2012118829 A2 | 9/2012 | |
| WO | 2013006608 A1 | 1/2013 | |
| WO | 2013006613 A1 | 1/2013 | |
| WO | 2013029009 A1 | 2/2013 | |
| WO | WO-2013035113 A1 * | 3/2013 | A61K 31/573 |
| WO | 2013063354 A1 | 5/2013 | |
| WO | 2013138073 A1 | 9/2013 | |
| WO | 2013138075 A1 | 9/2013 | |
| WO | 2014028847 A1 | 2/2014 | |
| WO | 2014134502 A1 | 9/2014 | |
| WO | 2015021382 A2 | 2/2015 | |
| WO | 2016007834 A1 | 1/2016 | |

(56) References Cited

FOREIGN PATENT DOCUMENTS

| WO | 2016010988 A1 | 1/2016 |
|---|---|---|
| WO | 2016022170 A1 | 2/2016 |
| WO | 2016160089 A1 | 10/2016 |
| WO | 2017011031 A1 | 1/2017 |
| WO | 2017019614 A1 | 2/2017 |
| WO | 2017151905 A1 | 9/2017 |
| WO | 2017180822 A1 | 10/2017 |
| WO | 2018189687 A1 | 10/2018 |
| WO | 2018236806 A1 | 12/2018 |
| WO | 2019169221 A1 | 9/2019 |
| WO | 2019232166 A1 | 12/2019 |

OTHER PUBLICATIONS

Watanabe et al. (J. Pharmacobio-Dyn. 1986;9:526-531) (Year: 1986).*
WITEPSOL® Fatty bases for suppositories [online] retrieved on Jul. 7, 2021 from: https://www.pharmacompass.com/pAssets/pdf/edqm/application/witepsol.pdf; 25 pages) (Year: 2021).*
Buffers (Calbiochem® [online] retrieved on Jul. 7, 2021 from: https://www.med.unc.edu/pharm/sondeklab/wp-content/uploads/sites/868/2018/10/buffers_calbiochem.pdf; 33 pages). (Year: 2021).*
Ansel et al. (Pharmaceutical Dosage Forms and Drug Delivery Systems 7th Edition 1999; pp. 279, 282 and 283; 4 pages total) (Year: 1999).*
International Search Report and the Written Opinion of the International Searching Authority corresponding to International Patent Application No. PCT/US2019/020209 (9 pages) (dated Apr. 30, 2019).
Amadeu et al. "Nitric Oxide Donor Improves Healing if Applied on Inflammatory and Proliferative Phase" Journal of Surgical Research, 149(1):84-93 (2008).
Bohl Masters et al. "Effects of nitric oxide releasing poly(vinyl alcohol) hydrogel dressings on dermal wound healing in diabetic mice" Wound Repair and Regeneration, 10(5):286-294 (2002).
Boykin et al. "HBO Mediates Increased Nitric Oxide Production Associated With Wound Healing" Wound Repaid and Regeneration 12(2):A15 (Abstract 054) (2004).
Hetrick et al. "Anti-biofilm efficacy of nitric oxide-releasing silica nanoparticles" Biomaterials, 30(14):2782-2789 (2009).
Keefer, Larry K. "Fifty Years of Diazeniumdiolate Research. From Laboratory Curiosity to Broad-Spectrum Biomedical Advances" ACS Chemical Biology, 6:1147-1155 (2011).
Extended European Search Report corresponding to European Patent Application No. 19760038.0 (8 pages) (dated Nov. 12, 2021).

* cited by examiner

NITRIC OXIDE RELEASING SUPPOSITORIES AND METHODS OF USE THEREOF

RELATED APPLICATION INFORMATION

This application claims the benefit of U.S. Provisional Patent Application Ser. No. 62/637,120, filed Mar. 1, 2018, the disclosure of which is incorporated herein by reference in its entirety.

FIELD

The present invention relates generally to suppositories and methods of using the same. Methods of using the suppositories include methods of treating and/or preventing an infection (e.g., a viral infection).

SUMMARY

It is noted that aspects described with respect to one embodiment may be incorporated in different embodiments although not specifically described relative thereto. NO-releasing suppositories (e.g., vaginal suppositories) are described herein. Some embodiments are directed to compositions, kits, and/or methods for treating and/or preventing an infection (e.g., a viral infection). In some embodiments, a method of treating and/or preventing a viral infection in a subject in need thereof is provided.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, is meant to include X as well as variations of ±20%, +10%, ±5%, 1%, ±0.5%, or even ±0.1% of X. A range provided herein for a measurable value may include any other range and/or individual value therein.

As used herein, the terms "increase," "increases," "increased," "increasing," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

According to some embodiments of the present invention provided herein is a nitric oxide (NO) releasing suppository (e.g., vaginal suppository). A vaginal suppository of the present invention may be a dosage form that comprises a solid body that can be inserted and/or placed into a vagina of a subject and may melt, soften, and/or dissolve upon insertion and/or placement. In some embodiments, a vaginal suppository may be inserted into a vagina with an applicator and/or without the use of an applicator. In some embodiments, a vaginal suppository of the present invention may be administered digitally. In some embodiments, a vaginal suppository may be inserted into a vagina with an applicator that is FDA CCS Guidance and USP compliant. In some embodiments, a vaginal suppository of the present invention may be administered by the subject to their vagina and/or may be administered to a subject without the need of a clinician (e.g., doctor) to administer.

In some embodiments, a suppository of the present invention is prepared by compression or molding or any other technique known to the skilled artisan. A suppository of the present invention may comprise one or more (e.g., 1, 2, 3, 4, or more) active pharmaceutical ingredient(s) dispersed and/or dissolved in one or more (e.g., 1, 2, 3, 4, or more) base(s) (i.e., suppository base) and optionally one or more (e.g., 1, 2, 3, 4, or more) excipient(s). In some embodiments, a vaginal suppository of the present invention includes a NO-releasing active pharmaceutical ingredient (API) and a suppository base. The vaginal suppository may also include one or more excipients such as, for example, a buffering agent, a preservative, a solvent, and/or a lubricant. An excipient may be one that does not adversely alter the vaginal suppository residence time in the vagina, tolerability and/or toxicological profile on application. In some embodiments, a vaginal suppository has a composition and/or pH that can provide and/or is configured to provide substantially all (e.g., at least about 75%) or complete (i.e., 100%) NO release from the vaginal suppository. In some embodiments, the amount of NO release from a vaginal suppository of the present invention upon administration to a subject is compared to the amount of NO release in vitro, which may optionally be tested in vitro by contact with a composition to comparable to physiological fluid the vaginal suppository may be contacted with in vivo.

In some embodiments, a suppository base and/or excipient of a vaginal suppository of the present invention may be selected to enable easy dispersion and/or at least partial solubilization of an API (e.g., dispersion and/or solubilization of the API at low temperatures such as, e.g., below 30° C. (e.g., from about 30-50° C., 35-40° C., or 45-50° C.)). In some embodiments, a suppository base and/or excipient of a vaginal suppository of the present invention may not promote degradation of the API and/or may not promote release of NO during manufacturing and/or storage. In some embodiments, a suppository base and/or excipient of a vaginal suppository of the present invention may maintain the amorphic form of the API and/or does not promote crystallization. In some embodiments, at least a portion of the API in a vaginal suppository of the present invention may be present in crystalline form. In some embodiments, a vaginal suppository of the present invention and/or a suppository base and/or excipient thereof may not alter vaginal microbiome (e.g., may not alter the number of microbes, pH, etc. by more than ±20% compared to the number of microbes, pH, etc. prior to administration). In some embodiments, a vaginal suppository of the present invention and/or a suppository base and/or excipient thereof may promote growth of beneficial vaginal microbes.

Suppository bases are classified into oleaginous (i.e., fatty) bases and water-soluble/water-miscible bases. Oleaginous (i.e., fatty) bases include, but are not limited to, *theobroma* oil (i.e., cocoa butter) and triglyceride, monoglyceride and diglyceride esters of $C_8$-$C_{20}$ fatty acids and the mixtures thereof. Examples of these fatty acids include, but are not limited to, capric acid, caprylic acid, eicosenoic acid, stearic acid, lauric acid, myristic acid, oleic acid, palmitic acid, ricinoleic acid and their derivatives. In some embodiments, a fatty base may be prepared from its natural source (e.g., coconut oil, palm oil and the like) and/or may be mixed with various additives. Examples of trade names for fatty bases include, but are not limited to, Suppocire®, Ovucire®, Japocire®, Witepsol®, Massa Estarinum®, Wecobee®, Fattibase®, Dehydag®, Hydrokote®, and Novata®.

Water-soluble/water-miscible bases include, but are not limited to, gelatin (e.g., glycerinated gelatin), polyethylene glycol (PEG), and glycerolated glycerin. In some embodiments, a suppository base of the present invention may include both a fatty base and a water-soluble/water-miscible base.

In some embodiments, a suppository base may be present in a vaginal suppository of the present invention in an amount of about 0.1% to about 99.9% by weight of the vaginal suppository. In some embodiments, a suppository base may be present in an amount of about 0.1% to about 1%, about 0.1% to about 5%, about 0.1% to about 10%, about 0.1% to about 20%, about 1% to about 10%, about 1% to about 20%, about 20% to about 30%, about 30% to about 40%, about 40% to about 50%, about 50% to about 60%, about 60% to about 70%, about 70% to about 99.9%, about 70% to about 95%, about 70% to about 90%, about 70% to about 85%, about 70% to about 80%, about 70% to about 75%, about 80% to about 90%, or about 90% to about 99.9% by weight of the vaginal suppository. In some embodiments, a suppository base may be present in an amount of no less than 70%, 75%, 80%, 85%, 90%, or 95% by weight of the vaginal suppository. For example, in some embodiments, a suppository base may be present in a vaginal suppository of the present invention in an amount of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9% by weight of the vaginal suppository.

In some embodiments, a suppository base in a suppository of the present invention may be hydrophobic (e.g., completely hydrophobic). In some embodiments, a suppository base in a suppository of the present invention may be hydrophilic (e.g., a PEG based suppository base and/or glycerol-gelatin). In some embodiments, a suppository base may have a low acid value, which may reduce and/or prevent premature release of nitric oxide (e.g., during manufacturing and/or storage). For example, a suppository base may have an acid value of less than about 3 mg KOH/g such as, e.g., less than about 2.5 mg KOH/g, less than about 2 mg KOH/g, less than about 1.5 mg KOH/g, less than about 1 mg KOH/g, less than about 0.5 mg KOH/g, or less than about 0.2 mg KOH. In some embodiments, a suppository base may be soluble or dispersible in water and/or may melt at body temperature.

In some embodiments, a buffering agent may be present in a vaginal suppository of the present invention in an amount of about 0.1% to about 30% by weight of the vaginal suppository. For example, in some embodiments, a buffering agent may be present in a vaginal suppository of the present invention in an amount of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the vaginal suppository. In some embodiments, two or more buffering agents may be present in a vaginal suppository of the present invention, and each of the two or more buffering agents may be present in a vaginal suppository of the present invention in an amount of about 0.1% to about 15% by weight of the vaginal suppository (e.g., about 0.1%, 0.5%, 1%, 2%, 3%, 4%, 5%, 6%, 7%, 8%, 9%, 10%, 11%, 12%, 13%, 14%, or 15% by weight of the vaginal suppository).

Exemplary buffering agents include, but are not limited to, potassium phosphate monobasic, phosphoric acid, citric acid, acetic acid, lactic acid, boric acid, succinic acid, malic acid, sodium citrate dihydrate, and any combination thereof. In some embodiments, a buffering agent (e.g., an acetate buffer) may have strong buffering capacity at physiological vaginal pH. In some embodiments, a vaginal suppository and/or a buffering agent present in a vaginal suppository may have a buffering capacity from about 50, 100, 200, or 300 µmol/g to about 400, 500, 600, or 700 µmol/g. In some embodiments, a vaginal suppository and/or a buffering agent present in a vaginal suppository has a buffering capacity of about 50, 100, 150, 200, 250, 300, 350, 400, 450, 500, 550, 600, 650, or 700 µmol/g.

In some embodiments, a preservative may be present in a vaginal suppository of the present invention in an amount of about 0.1% to about 2% by weight of the vaginal suppository, such as, but not limited to, about 0.1% to about 1% or about 0.1% to about 2% by weight of the vaginal suppository. In some embodiments, a preservative is present in a vaginal suppository in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the vaginal suppository.

Exemplary preservatives that may be present in a vaginal suppository include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

In some embodiments, a solvent may be present in a vaginal suppository of the present invention in an amount of about 0.1% to about 99.8% by weight of the vaginal suppository, such as, but not limited to, about 0.1% to about 1%, about 0.1% to about 5%, about 0.1% to about 10%, about 0.1% to about 20%, about 1% to about 10%, about 1% to about 20%, about 20% to about 30%, about 30% to about 40%, about 40% to about 50%, about 50% to about 60%, about 60% to about 70%, about 70% to about 80%, about 80% to about 90%, or about 90% to about 99.8% by weight of the vaginal suppository. In some embodiments, a solvent may be present in a vaginal suppository of the present invention in an amount of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.8% by weight of the vaginal suppository.

Exemplary solvents include, but are not limited to, acetone, methyl alcohol, ethanol, isopropanol, butyl alcohol, ethyl acetate, dimethyl isosorbide, propylene glycol, glycerin, ethylene glycol, polyethylene glycol, diethylene glycol monoethyl ether, water (e.g., purified and/or sterile water) and mixtures thereof. In some embodiments, the solvent in a vaginal suppository of the present invention may be glycerin.

In some embodiments, a lubricant may be present in a vaginal suppository of the present invention. A lubricant may aid in reducing friction between a surface of a vagina of a subject and a vaginal suppository during and/or after administration of the vaginal suppository into the vagina of the subject. In some embodiments, a lubricant may be present in a vaginal suppository of the present invention an amount of about 1% to about 10% by weight of the vaginal suppository. For example, in some embodiments, a lubricant may be present in a vaginal suppository of the present invention in an amount of about 1%, 2%, 3%, 4%, 5%, 6%, 7%, 8%, 9%, or 10% by weight of the vaginal suppository.

Exemplary lubricants include, but are not limited to, magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and mineral oil (e.g., light mineral oil), or combinations thereof. In some embodiments, a lubricant may enhance and/or improve the manufacturing of a suppository.

In some embodiments, mineral oil and/or hard waxes may be present in a vaginal suppository of the present invention and may improve handling during manufacturing. In some embodiments, mineral oil may be present in a vaginal suppository of the present invention in an amount of about 1% to about 10% or about 1% to about 20% by weight of the vaginal suppository. For example, in some embodiments, mineral oil may be present in a vaginal suppository of the present invention in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the vaginal suppository. In some embodiments, one or more hard waxes (e.g., 1, 2, 3, 4) may be present in a vaginal suppository of the present invention in an amount of about 1% to about 10% or about 1% to about 20% by weight of the vaginal suppository. For example, in some embodiments, one or more hard waxes may be present in a vaginal suppository of the present invention in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the vaginal suppository.

In some embodiments, a vaginal suppository of the present invention comprises an excipient, prebiotic, probiotic and/or symbiotic, which may enhance tolerability and/or conform to the FDA Guidance on Vaginal Microbicides. In some embodiments, an excipient, prebiotic, probiotic and/or symbiotic may be present in a vaginal suppository of the present invention in an amount sufficient to enhance tolerability, provide a therapeutic effect, and/or enhance vaginal microbiome health and/or growth (e.g., normal microbiome growth and/or numbers).

In some embodiments, a NO-releasing API may be present in a vaginal suppository of the present invention in an amount of about 0.1% to about 70% by weight of the vaginal suppository. For example, in some embodiments, a NO-releasing API may be present in a vaginal suppository of the present invention in an amount of about 0.1% to about 10%, about 0.1% to about 20%, about 20% to about 30%, about 30% to about 40%, about 40% to about 50%, about 50% to about 60%, or about 60% to about 70% by weight of the vaginal suppository. In some embodiments, a NO-releasing API may be present in a vaginal suppository of the present invention in an amount of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65% or 70% by weight of the vaginal suppository.

"Nitric oxide releasing active pharmaceutical ingredient" and "NO-releasing API," as used herein, refer to a compound or other composition that provides nitric oxide to the skin (e.g., mucosa) and/or tissue of a subject, but is not gaseous nitric oxide. In some embodiments, the NO-releasing API is also not acidified nitrite. In some embodiments, the NO-releasing API includes a nitric oxide-releasing compound, hereinafter referred to as a "NO-releasing compound." An NO-releasing compound includes at least one NO donor, which is a functional group that may release nitric oxide under certain conditions.

Any suitable NO-releasing compound may be used. In some embodiments, the NO-releasing compound includes a small molecule compound that includes an NO donor group. "Small molecule compound" as used herein is defined as a compound having a molecular weight of less than 500 Daltons, and includes organic and/or inorganic small molecule compounds. In some embodiments, the NO-releasing compound includes a macromolecule that includes an NO donor group. A "macromolecule" is defined herein as any compound that has a molecular weight of 500 Daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 μm and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in a vaginal suppository as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Pat. Nos. 8,282,967, 8,962,029 or 8,956,658, the disclosures of which are incorporated by reference herein in their entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the present invention, a nitric oxide-releasing active pharmaceutical ingredient may include NO-loaded precipitated silica. The NO-loaded precipitated silica may be formed from nitric oxide donor modified silane monomers into a co-condensed siloxane network. In one embodiment of the present invention, the nitric oxide donor may be an N-diazeniumdiolate. In some embodiments of the present invention, the nitric oxide-releasing active pharmaceutical ingredient may comprise, consist essentially of, or consist of a co-condensed siloxane network comprising a diazeniumdiolate (e.g., a N-diazeniumdiolate).

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors. In some embodiments of the present invention, the nitric oxide-releasing active pharmaceutical ingredient may comprise, consist essentially of, or consist of a co-condensed silica network synthesized from the condensation of a silane mixture comprising an alkoxysilane and at least one aminoalkoxysilane having an amine substituted by a diazeniumdiolate (e.g., a N-diazeniumdiolate).

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''-(NH-R')_n-Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethyl aminomethyl) phenethyltrimethoxysilane (AEMP3); [3-(methylamino)propyl]trimethoxysilane (MAP3); N-butylamino-propyltrimethoxysilane(n-BAP3); t-butylamino-propyltrimethoxysilane(t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: NH [R'—Si(OR)3]2, wherein R is alkyl and R' is alkylene. In some embodiments, the aminoalkoxysilane may be selected from bis(3-triethoxysilylpropyl)amine, bis[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R"—N(NONO—X+)—R'—Si(OR)$_3$, wherein R is alkyl, R' is alkylene or aralkylene, W' is alkyl or alkylamine, and X+ is a cation selected from the group consisting of Na+, K+ and Li+.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of R"—N(NONO—X+)—R'—Si(OR)$_3$, wherein: R is alkyl, R' is alkylene or aralkylene, R" is alkyl or alkylamine, and X+ is a cation selected from the group consisting of Na+ and K+.

In some embodiments, the NO-releasing API may comprise a co-condensed silica network comprising diazeniumdiolated aminoethylaminopropyl trimethoxy silane (AEAP3) and tetra methyl orthosilicate (TMOS) and/or a co-condensed silica network comprising diazeniumdiolated aminoethylaminopropyl trimethoxy silane (AEAP3) and tetraethyl orthosilicate (TEOS). In some embodiments, the NO-releasing API may comprise a co-condensed silica network comprising diazeniumdiolated methylaminopropyl trimethoxysilane (MAP3) and tetra methyl orthosilicate (TMOS) and/or a co-condensed silica network comprising diazeniumdiolated methylaminopropyl trimethoxysilane (MAP3) and tetraethyl orthosilicate (TEOS). In some embodiments, the NO-releasing API may comprise a co-condensed silica network comprising diazeniumdiolated methylaminopropyl trimethoxysilane (MAP3), ethylaminoisobutylsiloxane (EAIB3), and tetraethyl orthosilicate (TEOS). In some embodiments, the NO-releasing API may be ethylaminoisobutylsiloxane/methylaminopropylsiloxane-co-polysiloxane (EAIB3:MAP3-NONOate/TEOS). In some embodiments, the NO-releasing API may comprise an amorphous polymer.

In some embodiments of the invention, the particle size of a NO-releasing API may be in a range of about 20 nm to about 20 μm or any range therein, such as, but not limited to, about 100 nm to about 20 μm or about 1 μm to about 20 μm. The particle size may be tailored to minimize or prevent toxicity and/or penetration through the epidermis (or compromised dermis) and into the blood vessels. In particular embodiments, the particle size is distributed around a mean particle size of less than 20 μm, or any range therein, and the size may allow the particle to enter a follicle. In some embodiments, a NO-releasing API may have a particle size that is distributed around a mean particle size of about 20, 19, 18, 17, 16, 15, 14, 13, 12, 11, 10, 9, 8, 7, 6, 5, 4, 3, 2, or 1 μm. In further embodiments, a NO-releasing API may have a particle size that is distributed around a mean particle size of less than 10 μm, or any range therein, such as, but not limited to about 2 μm to about 10 μm or about 4 μm to about 8 μm. In other embodiments, the particle size may be distributed around a mean particle size of greater than 20 μm, or any range therein, and the size may prevent the particle from entering the follicle. In still further embodiments, a mixture of particles with mean particle sizes distributed around two or more mean particle sizes may be provided. A NO-releasing API may be micronized (e.g., ball and/or jet milled). Methods for providing a desired particle size and/or micronization include, but are not limited to, those described in U.S. Patent Application Publication No. 2013/0310533, which is incorporated herein by reference in its entirety.

In some embodiments, a NO-releasing API may have a low charge. In some embodiments, charge on a NO-releasing API may be controlled and/or modulated.

A vaginal suppository of the present invention may comprise a NO-releasing API and may store and/or release nitric oxide in an amount of about 0.01% to about 10% by weight of the vaginal suppository, such as, but not limited to, about 0.15% to about 2%, about 0.15% to about 1%, about 0.3% to about 1.2%, about 0.15% to about 6%, about 1% to about 10%, about 3% to about 6%, or about 1% to about 5% by weight of the vaginal suppository. In certain embodiments, a vaginal suppository of the present invention may comprise a nitric oxide-releasing active pharmaceutical and may store and/or release nitric oxide in an amount of about 0.01%, 0.05%, 0.1%, 0.15%, 0.3%, 0.6%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, or 10% by weight of the vaginal suppository. The amount of nitric oxide released may be determined using real time in vitro release testing. In some embodiments, nitric oxide release may be determined using a chemiluminescent nitric oxide analyzer.

A vaginal suppository of the present invention may release nitric oxide in an acidic environment. Upon administering (e.g., inserting and/or placing) a vaginal suppository of the present invention to a subject, the pH of the subject's vagina may be maintained below 7. In some embodiments, upon administering a vaginal suppository of the present invention to a subject, the pH of the subject's vagina may be maintained about below about 6, 5, 4, or 3. In some embodiments, upon administering a vaginal suppository of the present invention to a subject, the pH of the subject's vagina may be in a range of about 3.5 to about 4.8. In some embodiments, administration of a vaginal suppository of the present invention to a subject may not change the pH of the subject's vagina by more than 2 pH units. For example, administration of a vaginal suppository of the present invention to a subject may change the pH of the subject's vagina by 2 pH units or less such as, e.g., about 1.5, 1, 0.5, or 0 pH units.

In some embodiments, upon administering a vaginal suppository of the present invention to a subject, the subject's vagina may have a net alkalinity in a physiologically tolerable range and/or equal to the physiological net alkalinity in absence of a vaginal suppository of the present invention.

A vaginal suppository of the present invention may have no or reduced side effects and/or toxicity. In some embodiments, a vaginal suppository of the present invention has and/or provides no reproductive toxicity, no more than mild vaginal irritation, and/or no chromosomal aberration.

As used herein, the term "shelf life" refers to the length of time a vaginal suppository of the present invention maintains the ability to release a therapeutically effective amount of a therapeutic agent, such as, but not limited to, nitric oxide, in an unopened package stored under recommended storage conditions. The shelf life may, for example, be evidenced by the "use by" or "best if used by" date for the vaginal suppository, the manufacturer's expiration date of the vaginal suppository and/or the actual vaginal suppository characteristics after the specified period of time. Accordingly, the term "shelf life" as used herein should be construed as including both an "actual" shelf life of the vaginal suppository and a "predicted" shelf life of the vaginal suppository unless stated otherwise. As one skilled in the art will recognize, the rate of release of nitric oxide in a vaginal suppository under packaged and/or stored conditions may be different (i.e., faster or slower) than the rate of release of nitric oxide when the vaginal suppository is in use (e.g., administered to a subject). In certain embodiments, the rate of release of nitric oxide from a vaginal suppository of the present invention may be more rapid when the vaginal suppository is in use compared to the rate of release of nitric oxide when a vaginal suppository comprising the API was packaged and/or stored.

In some embodiments, shelf life may be determined by extrapolation of data at accelerated temperatures, such as, for example, by using the Arrhenius equation. In some embodiments, shelf life may be determined using linear regression analysis, such as, for example, when the kinetics of API degradation is not temperature dependent. In some embodiments, shelf life may be evaluated and/or determined by measuring the API (e.g., NO-releasing API), such as, for example, using high pressure liquid chromatography.

In some embodiments, the shelf life of the vaginal suppository is the time that the vaginal suppository maintains the ability to release at least 50% of the initial amount of nitric oxide that the vaginal suppository may release when packaged. In some embodiments, the shelf life of the vaginal suppository is the time that the vaginal suppository maintains the ability to release about 60%, at least 70%, at least 80%, at least 90%, at least 95%, or at least 98% of the initial amount of nitric oxide that the vaginal suppository may release when packaged. In some embodiments, the shelf life of the vaginal suppository is the time that the vaginal suppository maintains the ability to release a therapeutically effective amount of nitric oxide over a desired period of time. In some embodiments, the recommended storage conditions are room temperature. In some embodiments, the recommended storage conditions are refrigerated storage conditions. In particular embodiments, the refrigerated storage conditions are about 1° C. to about 12° C. or about 2° C. to about 8° C. In some embodiments, a packaged vaginal suppository may have a shelf life of at least about 1, 2, 3, 4, 5, 6, 7, 8, 9, 10, 11, 12, 13, 14, 15, 16, 17, 18, 19, 20, 21, 22, 23, or 24 months or more, or any range and/or individual value therein. In some embodiments, a vaginal suppository of the present invention may have a shelf life of at least about 2 years when stored at 25° C./60% relative humidity (RH) and/or a shelf life of at least about 6 Months when stored at 40° C./75% RH. In some embodiments, a vaginal suppository of the present invention may have a shelf life of at least about 2 years when stored at a temperature of about 2° C. to about 8° C. and/or a shelf life of at least about 6 months when stored at 25° C./60% RH.

Some embodiments may provide a packaged vaginal suppository of the present invention that has a useful life of at least about 7 days after opening the vaginal suppository. In some embodiments, the useful life is at least about 30 days, at least about 60 days, at least about 90 days, or at least about 1, 2, 3, 4, 5, 6, 8, or 9 months. In still further embodiments, the packaged vaginal suppository may have a useful life of from at least about 60 days to at least about 730 days. As used herein, the term "useful life" refers to the length of time that the vaginal suppository maintains the ability to release a therapeutically effective amount of nitric oxide from an opened packaged when applied as recommended and when stored under recommended storage conditions. The useful life may, for example, be evidenced by the manufacturer's recommended time to dispose of the vaginal suppository after opening or measurements of the vaginal suppositories characteristics after opening.

Accordingly, the term "useful life" as used herein should be construed as including both an "actual" useful life of the vaginal suppository or a "predicted" useful life of the vaginal suppository unless stated otherwise. In some embodiments, the useful life of the vaginal suppository is the time that the vaginal suppository maintains the ability to release at least 50% of the initial amount nitric oxide that the vaginal suppository may release when the vaginal suppository is opened. In further embodiments, the useful life of the vaginal suppository is the time that the vaginal suppository maintains the ability to release at least 70%, at least 80%, at least 90%, at least 95%, or at least 98% of the initial amount nitric oxide that the vaginal suppository may release when the vaginal suppository is opened. In some embodiments, the recommended storage conditions after opening are room temperature. In particular embodiments, the recommended storage conditions after opening are refrigerated conditions.

The rate of nitric oxide release from a vaginal suppository of the present invention may be controlled and/or modulated by accessibility of protons in the surrounding environment. In some embodiments, a vaginal suppository of the present invention may have a NO release rate, pattern, and/or amount as described in PCT/US2015/039908 and/or PCT/US2016/012668, the contents of each of which are incorporated herein by reference in their entirety. In some embodiments, a vaginal suppository of the present invention may release nitric oxide at a release rate suitable to allow and/or provide for NO to penetrate into and/or onto the tissue of the vagina upon administration and may be physiologically tolerable. In some embodiments, a vaginal suppository of the present invention may release nitric oxide at a release rate suitable to allow and/or provide for NO to penetrate into and/or onto cervical tissue of the subject upon administration of the vaginal suppository to the vagina of the subject.

In some embodiments, a vaginal suppository of the present invention may be a single phase system (i.e., a single unit dosage form). A single phase system may have a single layer or may have multiple layers (e.g., a buffer in an outer layer and API in an inner layer and/or core) present in the single unit dosage form. With a single phase system, a vaginal suppository of the present invention may release nitric oxide upon interaction and/or contact with physiological vaginal pH. In some embodiments, an API and proton source may be packaged in a single phase system of the present invention so that they only interact after administration of the vaginal suppository to a vagina of a subject. In some embodiments, a vaginal suppository of the present invention may be a dual phase system. With a dual phase system, an activator (e.g., a water or hydrogel based activator) that is separate from a vaginal suppository of the present invention may be used to initiate release of nitric oxide from the vaginal suppository.

In some embodiments, upon administering a vaginal suppository of the present invention to a subject, the vaginal suppository may melt and/or may form a film or coating on a surface of a vagina of the subject. In some embodiments, the vaginal suppository provides a film or coating on at least about 25%, 30%, 35%, 40%, 45%, 50%, 55%, 60%, 65%, 70%, 75%, 80%, 90%, 95%, or 100% of the vaginal surface for a subject. In some embodiments, the vaginal suppository provides a film or coating on a portion (e.g., 25%, 50%, 75%) or all (i.e., 100%) of a disease area on the vaginal surface for a subject. In some embodiments, upon administering a vaginal suppository of the present invention to a subject, the vaginal suppository provides a film or coating on at least about 5%, 10%, 15%, 20%, 25%, 30%, 35%, 40%, 45%, 50%, 55%, 60%, 65%, 70%, 75%, 80%, 90%, 95%, or 100% of cervical tissue for a subject. In some embodiments, a vaginal suppository of the present invention may have a suitable osmolarity. In some embodiments, a vaginal suppository of the present invention may have an osmolarity of about 10 mOsm/kg to about 8000 mOsm/kg or about 250 mOsm/kg to about 400 mOsm/kg. In some embodiments, a vaginal suppository of the present invention may have an osmolarity of about 10 mOsm/kg to about 100 mOsm/kg, about 100 mOsm/kg to about 200 mOsm/kg, about 200 mOsm/kg to about 300 mOsm/kg, about 300 mOsm/kg to about 400 mOsm/kg, about 400 mOsm/kg to about 500 mOsm/kg, about 500 mOsm/kg to about 600 mOsm/kg, about 600 mOsm/kg to about 700 mOsm/kg, about 700 mOsm/kg to about 800 mOsm/kg, about 800 mOsm/kg to about 900 mOsm/kg, about 900 mOsm/kg to about 1000 mOsm/kg, about 1000 mOsm/kg to about 2000 mOsm/kg, about 2000 mOsm/kg to about 3000 mOsm/kg, about 3000 mOsm/kg to about 4000 mOsm/kg, about 4000 mOsm/kg to about 5000 mOsm/kg, about 5000 mOsm/kg to about 6000 mOsm/kg, about 6000 mOsm/kg to about 7000 mOsm/kg, or about 7000 mOsm/kg to about 8000 mOsm/kg. For example, a vaginal suppository of the present invention may have an osmolarity of about 10, 50, 100, 150, 200, 250, 300, 350, 400, 450, 500, 550, 600, 650, 700, 750, 800, 850, 900, 950, 1000, 2000, 3000, 4000, 5000, 6000, 7000, or 8000 mOsm/kg.

In some embodiments, a vaginal suppository of the present invention may have a volume in a range of about 0.5 mL to about 5 mL. For example, a vaginal suppository of the present invention may have a volume of about 0.5 mL, 1 mL, 1.5 mL, 2 mL, 2.5 mL, 3 mL, 3.5 mL, 4 mL, 4.5 mL, or 5 mL.

In some embodiments, a vaginal suppository of the present invention may adhere and/or be mucoadhesive to a surface of the vagina. In some embodiments, a vaginal suppository of the present invention may have a mean residence time that is appropriate for activity, treatment, and/or dosing regimen. In some embodiments, a vaginal suppository of the present invention may have a mean residence time that is suitable to provide a therapeutic effect for a subject. In some embodiments, a vaginal suppository of the present invention may have a mean residence time that is of a duration to administer a treatment effective amount of the API and/or NO to the subject. In some embodiments, a vaginal suppository of the present invention may have a mean residence time that has a duration at least equivalent to the duration of time over which the vaginal suppository releases NO.

In some embodiments, a vaginal suppository of the present invention may be an anhydrous vaginal suppository. "Anhydrous," as used herein, means that there is no direct addition of water to the vaginal suppository when it is being prepared. However, those skilled in the art will recognize that water may be physically and/or chemically absorbed by the vaginal suppository and/or by one or more ingredients in the vaginal suppository at any time during the preparation, storage, and/or use of the vaginal suppository (i.e., indirect addition of water to the vaginal suppository). In some embodiments, the term "anhydrous" means that the vaginal suppository has a water content of less than 5% by weight of the vaginal suppository or any range and/or individual value therein. A vaginal suppository may have a water content of less than 5, 4.5, 4, 3.5, 3, 2.5, 2, 1.5, 1, or 0.5%, or any range therein, by weight of the vaginal suppository. Water content may be measured by methods known to those of skill in the art, such as, but not limited to, Karl Fischer titration.

According to some embodiments of the present invention, provided herein are methods for treating and/or preventing a viral, bacterial, protozoan, and/or fungal infection in and/or on a subject. In some embodiments, a vaginal suppository and/or method of the present invention may treat and/or prevent a viral, bacterial, protozoan, and/or fungal infection in and/or on a subject. In some embodiments, a vaginal suppository of the present invention may be antimicrobial (e.g., antiviral, antibacterial, and/or antifungal).

According to some embodiments of the present invention, provided herein are methods of treating and/or preventing an infection (e.g., a viral infection). A method of treating and/or preventing an infection (e.g., a viral infection) may comprise administering a vaginal suppository of the present invention to the vagina of a subject, thereby treating and/or preventing the infection in the subject. In some embodiments, the vaginal suppository may be administered by inserting, placing, and/or the like the vaginal suppository into the vagina of the subject. In some embodiments, a method of the present invention may suppress and/or inhibit viral replication of a virus and/or enhance the local immune response of a subject. In some embodiments, administration of the vaginal suppository may provide for topical and/or transdermal delivery of nitric oxide (NO) to the subject. In some embodiments, a method of the present invention may provide for targeted delivery of NO to the vagina of a subject or a portion thereof and/or may provide for local, systemic delivery of NO to the surrounding tissues and/or organs of the subject. In some embodiments, a method of administering a vaginal suppository of the present invention may administer NO to the tissue of a subject and/or through the tissue to a localized area.

Exemplary viral infections include, but are not limited to, a viral infection caused by cytomegalovirus (CMV), epstein-barr virus, herpes simplex virus (HSV 1+2), herpes zoster, human herpes virus 6 (HHV-6), human herpes virus 8 (HHV-8), papillomavirus, and/or molluscum contagiosum. In some embodiments, the viral infection may be caused by a papillomavirus, such as a human papillomavirus. The human papillomavirus (HPV) may be HPV type 1, 2, 3, 4, 6, 10, 11, 16, 18, 31, 33, 35, 39, 45, 51, 52, 56, 58, and/or 59. In some embodiments, the viral infection may be caused by a herpes simplex virus, such as herpes simplex type 1 and/or herpes simplex type 2. In some embodiments, the viral infection may infect the vaginal tissue and/or cervical tissue of the subject. In certain embodiments, the virus may be a human virus.

In some embodiments, a vaginal suppository of the present invention may be used to treat and/or prevent High Risk HPV mediated Cervical Intraepithelial Neoplasia (CIN). In some embodiments, a vaginal suppository and/or method of the present invention results in and/or provides a PCR Negative result for HPV using cervical brush after administration of and/or treatment with the vaginal suppository.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom associated with the condition (e.g., a viral infection) is achieved and/or there is a delay in the progression of the condition. In some embodiments, the severity of a condition such as, e.g., a viral infection (e.g., a viral infection caused by human papillomavirus), may be reduced in a subject compared to the severity of the condition in the absence of a method of the present invention. In certain embodiments, a method of the present invention treats a viral infection in a subject, such as a viral infection that has affected the vagina of the subject. In some embodiments, a method of the present invention may treat a viral infection by eliminating and/or reducing the size and/or appearance of at least one clinical symptom associated with the viral infection (e.g., a benign lesion). In some embodiments, a method of the present invention may treat a viral infection by eliminating at least one clinical symptom associated with the viral infection (e.g., a benign lesion) for a given period of time (e.g., 1, 2, 3, 4, 5, or 6 day(s), or 1, 2, 3, 4, or more weeks, etc.).

In some embodiments, a vaginal suppository of the present invention is administered in a treatment effective amount. A "treatment effective amount" and "therapeutically effective amount" are used interchangeably herein and refer to an amount that is sufficient to treat (as defined herein) a subject. Those skilled in the art will appreciate that the therapeutic effects need not be complete or curative, as long as some benefit is provided to the subject. In some embodiments, a treatment effective amount of a vaginal suppository of the present invention may be administered and may include administering a treatment effective amount of a nitric oxide-releasing active pharmaceutical ingredient. In some embodiments, a treatment effective amount of nitric oxide may be administered and/or applied in a method of the present invention. In some embodiments, a method of the present invention is carried out in a manner such that the administration of a vaginal suppository comprising a nitric oxide (NO)-releasing active pharmaceutical ingredient (API) does not produce systemic effects (e.g., adverse systemic effects) from the administration of nitric oxide, such as, for example, when the vaginal suppository, NO-releasing API, and/or NO is administered in a treatment effective amount. In some embodiments, a method of the present invention is carried out in a manner such that the administration of a vaginal suppository comprising a nitric oxide-releasing active pharmaceutical ingredient produces a local, systemic effect from the administration of nitric oxide, such as, for example, when the vaginal suppository, NO-releasing API, and/or NO is administered in a treatment effective amount.

The terms "prevent," "preventing" and "prevention" (and grammatical variations thereof) refer to avoidance, reduction and/or delay of the onset of a condition (e.g., a viral infection) and/or a clinical symptom associated therewith in a subject and/or a reduction in the severity of the onset of the condition and/or clinical symptom relative to what would occur in the absence of a method of the present invention. The prevention can be complete, e.g., the total absence of the condition and/or clinical symptom. The prevention can also be partial, such that the occurrence of the condition and/or clinical symptom in the subject and/or the severity of onset is less than what would occur in the absence of a method of the present invention. In certain embodiments, a method of the present invention prevents a viral infection in a subject, such as a viral infection that can affect the vagina of the subject.

In some embodiments, a vaginal suppository of the present invention is administered in a prevention effective amount. A "prevention effective" amount as used herein is an amount that is sufficient to prevent (as defined herein) the condition (e.g., viral infection) and/or clinical symptom in the subject. Those skilled in the art will appreciate that the level of prevention need not be complete, as long as some benefit is provided to the subject. In some embodiments, a prevention effective amount of a vaginal suppository of the present invention may be administered and may include administering a prevention effective amount of a nitric oxide-releasing active pharmaceutical ingredient. In some embodiments, a prevention effective amount of nitric oxide may be administered and/or applied in a method of the present invention. In some embodiments, a method of the present invention is carried out in a manner such that the administration of a vaginal suppository comprising a NO-releasing API does not produce systemic effects (e.g., adverse systemic effects) from the administration of nitric oxide, such as, for example, when the vaginal suppository, NO-releasing API, and/or NO is administered in a prevention effective amount. In some embodiments, a method of the present invention is carried out in a manner such that the administration of a vaginal suppository comprising a nitric oxide-releasing active pharmaceutical ingredient produces a local, systemic effect from the administration of nitric oxide, such as, for example, when the vaginal suppository, NO-releasing API, and/or NO is administered in a prevention effective amount.

A vaginal suppository of the present invention may be administered to a subject using any method known to those of skill in the art. In some embodiments, the vaginal suppository may be administered to the subject at least 1, 2, 3, or more times per day. In some embodiments, the vaginal suppository may be administered to the subject at least 1, 2, 3, 4, 5, 6, 7, 8, or more times per week and/or month. In certain embodiments, the vaginal suppository may be administered to the subject once daily, twice daily, every other day, every third day, once per week, or twice per week. In some embodiments, the vaginal suppository may be administered at least once daily for an extended period of time (e.g., a week, month, 2 months, etc.) and/or until the condition (e.g., viral infection) and/or clinical symptom associated therewith has been treated and/or prevented. In some embodiments, the vaginal suppository may be applied on an as needed basis.

The present invention finds use in both veterinary and medical applications. Suitable subjects of the present invention include, but are not limited to avians and mammals. The term "avian" as used herein includes, but is not limited to, chickens, ducks, geese, quail, turkeys, pheasants, parrots, parakeets, macaws, cockatiels, canaries, and finches. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), etc. In some embodiments, the subject is a mammal and in certain embodiments the subject is a human. Human subjects include both males and females and subjects of all ages including fetal, neonatal, infant, juvenile, adolescent, adult, and geriatric subjects.

The methods of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" or "in need thereof" a method of the present invention, for example, the subject is in an at-risk population (e.g. the subject may be at-risk for or more susceptible to a viral infection), the subject has findings typically associated with a viral infection, and/or the subject is suspected to be or to have been exposed to a virus. In some embodiments, a subject in need thereof has a viral infection and/or a clinical sign or symptom associated therewith that may be treated with a method of the present invention. The present invention may be particularly suitable for children, adolescents, adults, and/or geriatric subjects.

In some embodiments, a method of the present invention may prevent and/or reduce the appearance and/or size of a benign lesion. Exemplary benign lesions include, but are not limited to, a wart (e.g., genital warts, etc.), papillomata, molluscum contagiosum, and/or herpetic lesions. In some embodiments, the benign lesion may be induced and/or caused by a papillomavirus, such as a human papillomavirus.

A method of the present invention may reduce the appearance and/or size of a benign lesion by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the appearance and/or size of a benign lesion prior to administering of a vaginal suppository of the present invention. The appearance of the benign lesion may be evaluated visually, such as, but not limited to, by the subject and/or a physician. The size of the benign lesion may be determined using methods known to those of skill in the art. In some embodiments, a method of the present invention may prevent and/or reduce the appearance and/or size of a wart.

In certain embodiments, the subject may see a reduction in the size and/or appearance of a benign lesion within 1, 2, 3, 4, 5, 6, 7, 8, 9, 10, 11, 12, 13, or more day(s) and/or week(s). In some embodiments, the method may reduce the size and/or appearance of a benign lesion in the skin and/or tissue of the subject with 12 weeks or less, in some embodiments, within 8 weeks or less, and in further embodiments, within 4 weeks or less.

A method of the present invention may reduce the number of benign lesions by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of benign lesions prior to administering of a vaginal suppository of the present invention. The number of benign lesions may be evaluated visually, such as, but not limited to, by the subject and/or a physician. The number of benign lesions may be determined using methods known to those of skill in the art. In some embodiments, a method of the present invention may prevent and/or reduce the number of warts.

A method of the present invention may decrease the rate of recurrence of a benign lesion in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the same type of benign lesion in the absence of administering of a vaginal suppository of the present invention. The rate of recurrence may be determined using methods known to those of skill in the art. For example, after a treatment and/or removal of a benign lesion, the number of benign lesions may be visually determined after a given period of time to determine the rate of recurrence. In some embodiments, a method of the present invention may decrease the rate of recurrence of warts in a subject.

In certain embodiments, a method of the present invention may prevent and/or reduce the appearance and/or size of a premalignant lesion and/or a malignant lesion, such as, for example, a tumor. The premalignant lesion and/or malignant lesion may be caused by and/or induced by a viral infection. In some embodiments, a premalignant lesion and/or malignant lesion may be a premalignant and/or malignant cutaneous lesion. In some embodiments, the premalignant lesion and/or malignant lesion may be due to and/or caused by cancer of the cervix. In some embodiments, the premalignant lesion and/or malignant lesion may be induced and/or caused by a papillomavirus, such as a human papillomavirus. In some embodiments, a method of the present invention may prevent and/or reduce the appearance and/or size of cervical intraepithelial neoplasia.

A method of the present invention may reduce the appearance and/or size of a premalignant lesion and/or malignant by at least about 5%, 10%, 15%, 20%, 25%, 30%, 35%, 40%, 45%, 50%, 55%, 60%, 65%, 70%, 75%, 80%, 85%, 90%, 95%, 97% or more compared to the appearance and/or size of a premalignant lesion and/or a malignant lesion prior to administering of a vaginal suppository of the present invention. The appearance of the premalignant lesion and/or a malignant lesion may be evaluated visually, such as, but not limited to, by the subject and/or a physician. The size of the premalignant lesion and/or a malignant lesion may be determined using methods known to those of skill in the art.

A method of the present invention may reduce the number of premalignant lesions and/or malignant lesions by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of premalignant lesions and/or malignant lesions prior to administering of a vaginal suppository of the present invention. The number of premalignant lesions and/or malignant lesions may be evaluated visually, such as, but not limited to, by the subject and/or a physician. The number of premalignant lesions and/or malignant lesions may be determined using methods known to those of skill in the art.

A method of the present invention may decrease the rate of recurrence of a premalignant lesion and/or malignant lesion in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the same type of premalignant lesion and/or malignant lesion in the absence of administering of a vaginal suppository of the present invention. The rate of recurrence may be determined using methods known to those of skill in the art. For example, after a treatment and/or removal of a premalignant lesion and/or malignant lesion, the number of premalignant and/or malignant lesions may be visually determined after a given period of time to determine the rate of recurrence.

In some embodiments, a method of the present invention may administer nitric oxide to the basal layer of a subject's epithelium. A method of the present invention may administer a treatment effective and/or a prevention effective amount of nitric oxide to the basal layer of a subject's epithelium. In some embodiments, nitric oxide may be administered to the basement membrane of a subject's epithelium.

In some embodiments, a method of the present invention may administer nitric oxide in an amount sufficient to induce apoptosis or other cellular damage in virally infected cells. In some embodiments, a method of the present invention may administer nitric oxide in an amount sufficient to inhibit and/or prevent viral replication in virally infected cells. A method of the present invention may reduce viral replication by at least about 10%, 15%, 20%, 25%, 30%, 35%, 40%, 45%, 50%, 55%, 60%, 65%, 70%, 75%, 80%, 85%, 90%, 95%, 98%, 99%, or 100% compared to the rate of replication prior to the method of the present invention.

In some embodiments, a method of the present invention may treat and/or prevent a viral infection in a subject without cytotoxicity to host cells or with reduced cytotoxicity to host cells. The method may treat and/or prevent the viral infection in the subject with reduced host cell cytotoxicity compared to a different method for treating the viral infection, such as, for example, one that does not administer nitric oxide to the skin and/or tissue of a subject or one that uses acidified nitrite. In some embodiments, a method of the present invention may reduce host cell cytotoxicity by at least about 10%, 15%, 20%, 25%, 30%, 35%, 40%, 45%, 50%, 55%, 60%, 65%, 70%, 75%, 80%, 85%, 90%, 95%, 98%, 99%, or 100% compared to a different method for treating the viral infection. A method of the present invention may reduce and/or eliminate viral replication with no or minimal host cell cytotoxicity. For example, the method may provide a host cell cytotoxicity of about 50% or less (e.g., about 40%, 30%, 20%, 10%, 5%, or less). Cytotoxicity may be determined using methods known to those of skill in the art, such as, for example, a qualitative reading of hematoxylin & eosin (H&E) slides, a lactate dehydrogenase (LDH) assay and/or a 3-(4,5-Dimethyl-2-thiazolyl)-2,5-diphenyl-2H-tetrazolium bromide (MTT) assay. In some embodiments, a method of the present invention may not cause apoptosis. For example, the method may not cause apoptosis in keratinocyte layers of the skin and/or tissue.

In some embodiments, a method of the present invention may cause cells in the skin and/or tissue to normalize. The cells may be those that received a therapeutic and/or prophylactic effect from a method of the present invention. For example, the cells may be those that were administered nitric oxide according to a method of the present invention. The cells may normalize by, for example, returning to a normal growth rate and/or may complete differentiation. In some embodiments, a method of the present invention may reduce the number of actively dividing cells throughout the skin and/or tissue and may cause cellular division to be restricted to the basal layer of the skin and/or tissue as is the normal physiologic state. In some embodiments, a method of the present invention may return cells in the skin and/or tissue to a growth rate that does not cause the cells, skin, and/or tissue to display hyperproliferation, hyperplasia (e.g., benign hyperplasia), and/or dysplasia.

In some embodiments, the virus may cause a thickening in an area of the skin (e.g., the virus may lead to a wart on the skin) and/or tissue and a method of the present invention may reduce the thickness of the skin and/or tissue in this area, such as by at least about 10%, 15%, 20%, 25%, 30%, 35%, 40%, 45%, 50%, or more and/or may return the thickness of the skin and/or tissue in this area to a normal thickness. In some embodiments, the method may reduce the thickness of a thickened area of skin and/or tissue and/or return the thickness of the skin and/or tissue in the thickened area to a thickness of about 20% or less than the normal thickness of the skin and/or tissue. For example, an area of normal skin may have a thickness of 2 mm and a method of present invention may reduce the thickness of thickened skin in this area to a thickness in a range of about 2.4 mm to about 2 mm.

In some embodiments, a method of the present invention may cause cells in the skin and/or tissue to return to a normal G2 and/or S phase. For example, a virus may cause cells to have a prolonged G2 phase following S phase reentry. In some embodiments, a method of the present invention may disrupt and/or interfere with a protein involved in viral replication. For example, a method of the present invention may disrupt and/or interfere with an E7 and/or E6 protein and/or its interactions and/or signaling. In some embodiments, a method of the present invention may reduce the amount of and/or activation of an E6 and/or E7 viral protein. In some embodiments, a method of the present invention may activate and/or increase a cellular process that prohibits and/or decreases viral replication.

In some embodiments, a method of the present invention may reduce the amount of viral DNA in virally infected cells and/or the vagina of a subject. For example, a method of the present invention may reduce the amount of viral DNA by at least about 10%, 15%, 20%, 25%, 30%, 35%, 40%, 45%, 50%, 55%, 60%, 65%, 70%, 75%, 80%, 85%, 90%, 95%, 98%, 99%, or 100% compared to the amount of viral DNA present prior to the method of the present invention.

The present invention is explained in greater detail in the following non-limiting Examples.

EXAMPLES

Example 1

| Ingredient | % w/w | Functionality |
| --- | --- | --- |
| NVN3100 (a NO-releasing compound) | 0.1-10 | API |
| Ovucire ®/Suppocire ®/Japocire ® | 0.1-99.9 (or quantity sufficient (QS) to 100) | Suppository base |

Ovucire®/Suppocire®/Japocire® are hard fat based suppository bases that are used to disperse the active ingredient (NVN3100). These suppository bases can melt in the vaginal cavity and release the drug suspended in the base.

The suppository bases selected are hydrophobic as presence of moisture can release nitric oxide from NVN3100. The suppository bases selected have a low acid value to minimize release of nitric oxide in manufacturing and/or during storage. In some embodiments, the suppository base is present in an amount of no less than 90% by weight of the suppository.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

Example 2

| Ingredient | % w/w | Functionality |
| --- | --- | --- |
| NVN3100 | 0.1-10 | API |
| Gelatin | 0.1-20 | Suppository base |
| Glycerin | 0.1-99.8 (or QS to 100) | Solvent |

The melting range of the suppository may be tuned using a glycero gelatin suppository. Glycerin may help disperse and/or dissolve the API. The ratio of gelatin to glycerin will be selected so that there is minimal moisture. Care will be taken to minimize entrapment of moisture in the suppository. In some embodiments, the API may be coated to enable using a glycerol-gelatin suppository base. For example, in some embodiments, microencapsulation may be used to minimize degradation of the API and/or premature release of NO from the API. In some embodiments, glycerin is present in an amount of no less than 70% by weight of the suppository.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, hard waxes optionally in an amount of about 1 to about 10% by weight of the suppository, and/or one or more additional solvents (e.g., purified water) optionally in an amount of about 1 to about 10% by weight of suppository.

Example 3

| Ingredient | % w/w | Functionality |
| --- | --- | --- |
| NVN3100 | 0.1-10 | API |
| Cocoabutter or other waxy base | 0.1-99.9 (or QS to 100) | Suppository base |

Cocoa butter (*Theobroma* oil) is waxy base composed of triglycerides of fatty acids and has a melting point in the range of about 31° C. to about 34° C. In some embodiments, a waxy base (e.g., cocoa butter) is present in an amount of no less than 90% by weight of the suppository.

Care will be taken to minimize overheating of the base during manufacturing as the base has propensity to convert into polymorphs that have different physicochemical characteristics. Identifying the source with lower free fatty acids may enhance the stability of the API dispersed in the base.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

Example 4

| Ingredient | % w/w | Functionality |
| --- | --- | --- |
| NVN3100 | 0.1-10 | API |
| Ovucire ®/Suppocire ®/Japocire ® | 0.1-99.6 (or QS to 100) | Suppository base |
| Sodium Citrate Dihydrate | 0.1-12 | Buffering Agent |
| Citric Acid | 0.1-12 | Buffering Agent |
| Benzyl Alcohol or another similar preservative | 0.1-2 | Preservative |

This suppository may be a single-phase unit dose suppository that can co-deliver the API and the proton source, which may provide for easy and/or increased patient compliance. In some embodiments, the suppository base is present in an amount of no less than 60% by weight of the suppository.

Hard fat based suppository bases will be selected that minimize interactions of the API and one or more buffering agent(s). The buffering agents can be selected to have strong buffering capacity at physiological vaginal pH and to be physiologically tolerable buffers.

Alternatively, the suppository may be designed and manufactured to be a multi-layered single phase system where the API is stored in the core and the buffering agents are in an outer layer around the core. On insertion into the vaginal cavity, the base melts releasing the buffering agents, which provide the protons needed for releasing nitric oxide from the API that is dispersed in the core.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

Example 5

| Ingredient | % w/w | Functionality |
| --- | --- | --- |
| NVN3100 | 0.1-10 | API |
| Glycerogelatin base | 0.1-99.6 (or QS to 100) | Suppository base |
| Sodium Citrate Dihydrate | 0.1-12 | Buffering Agent |
| Citric Acid | 0.1-12 | Buffering Agent |
| Benzyl Alcohol or other related preservative | 0.1-2 | Preservative |

This suppository may be a single-phase unit dose suppository that can co-deliver the API and the proton source, which may provide for easy and/or increased patient compliance. In some embodiments, the suppository base is present in an amount of no less than 60% by weight of the suppository.

Glycero gelatin bases will be manufactured in the suppository to minimize interaction of the API and one or more buffers. The buffering agents can be selected to have strong buffering capacity at physiological vaginal pH and to be physiologically tolerable buffers.

The suppository may be a multi-layered single phase system where the API is stored in the core and one or more buffering agents are in an outer layer, which may rapidly disperse and/or melt. On insertion into the vaginal cavity the suppository base may melt and/or disperse, thereby releasing the buffering agent(s), which can provide protons that can be used to release NO from the API dispersed in the core.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

Example 6

| Ingredient | % w/w | Functionality |
|---|---|---|
| NVN3100 | 0.1-10 | API |
| Cocoabutter or waxy base | 0.1-99.6 (or QS to 100) | Suppository base |
| Sodium Citrate Dihydrate | 0.1-12 | Buffering Agent |
| Citric Acid | 0.1-12 | Buffering Agent |
| Benzyl Alcohol or other similar preservative | 0.1-2 | Preservative |

This suppository may be a single-phase unit dose suppository that can co-deliver the API and the proton source, which may provide for easy and/or increased patient compliance. In some embodiments, the suppository base is present in an amount of no less than 60% by weight of the suppository.

Cocoa butter bases will be manufactured in the suppository to minimize interaction of the API and one or more buffers. The buffering agents can be selected to have strong buffering capacity at physiological vaginal pH and to be physiologically tolerable buffers.

The suppository may be a multi-layered single phase system where the API is stored in the core and one or more buffering agents are in an outer layer, which may rapidly disperse and/or melt. On insertion into the vaginal cavity the suppository base may melt and/or disperse, thereby releasing the buffering agent(s), which can provide protons that can be used to release NO from the API dispersed in the core.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

Example 7

| Ingredient | % w/w | Functionality |
|---|---|---|
| NVN3100 | 0.1-10 | API |
| Ovucire ®/Suppocire ®/Japocire ® | 0.1-99.6 (or QS to 100) | Suppository base |
| Potassium Phosphate Monobasic | 0.1-12 | Buffering Agent |
| Citric Acid | 0.0-4 | Buffering Agent |
| Benzyl Alcohol or another similar preservative | 0.1-2 | Preservative |

This suppository may be a single-phase unit dose suppository that can co-deliver the API and the proton source, which may provide for easy and/or increased patient compliance. In some embodiments, the suppository base is present in an amount of no less than 70% by weight of the suppository.

Hard fat based suppository bases will be selected that minimize interactions of the API and one or more buffering agent(s). The buffering agents can be selected to have strong buffering capacity at physiological vaginal pH and to be physiologically tolerable buffers. In some embodiments, citric acid is not present in the suppository, so the buffer comprises a phosphate buffering agent. In some embodiments, both citric acid and potassium phosphate monobasic are present in the suppository.

Alternatively, the suppository may be designed and manufactured to be a multi-layered single phase system where the API is stored in the core and the buffering agents are in an outer layer around the core. On insertion into the vaginal cavity, the base melts releasing the buffering agents, which provide the protons needed for releasing nitric oxide from the API that is dispersed in the core.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

Example 8

| Ingredient | % w/w | Functionality |
|---|---|---|
| NVN3100 | 0.1-10 | API |
| Glycerogelatin base | 0.1-99.6 (or QS to 100) | Suppository base |
| Potassium Phosphate Monobasic | 0.1-12 | Buffering Agent |
| Citric Acid | 0.0-4 | Buffering Agent |
| Benzyl Alcohol or other related preservative | 0.1-2 | Preservative |

This suppository may be a single-phase unit dose suppository that can co-deliver the API and the proton source, which may provide for easy and/or increased patient compliance. In some embodiments, the suppository base is present in an amount of no less than 70% by weight of the suppository.

Glycero gelatin bases will be manufactured in the suppository to minimize interaction of the API and one or more buffers. The buffering agents can be selected to have strong buffering capacity at physiological vaginal pH and to be physiologically tolerable buffers. In some embodiments, citric acid is not present in the suppository, so the buffer comprises a phosphate buffering agent. In some embodiments, both citric acid and potassium phosphate monobasic are present in the suppository.

The suppository may be a multi-layered single phase system where the API is stored in the core and one or more buffering agents are in an outer layer, which may rapidly disperse and/or melt. On insertion into the vaginal cavity the suppository base may melt and/or disperse, thereby releasing the buffering agent(s), which can provide protons that can be used to release NO from the API dispersed in the core.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

Example 9

| Ingredient | % w/w | Functionality |
| --- | --- | --- |
| NVN3100 | 0.1-10 | API |
| Cocoabutter or waxy base | 0.1-99.6 (or QS to 100) | Suppository base |
| Potassium Phosphate Monobasic | 0.1-12 | Buffering Agent |
| Citric Acid | 0.0-4 | Buffering Agent |
| Benzyl Alcohol or other similar preservative | 0.1-2 | Preservative |

This suppository may be a single-phase unit dose suppository that can co-deliver the API and the proton source, which may provide for easy and/or increased patient compliance. In some embodiments, the suppository base is present in an amount of no less than 70% by weight of the suppository.

Cocoa butter bases will be manufactured in the suppository to minimize interaction of the API and one or more buffers. The buffering agents can be selected to have strong buffering capacity at physiological vaginal pH and to be physiologically tolerable buffers. In some embodiments, citric acid is not present in the suppository, so the buffer comprises a phosphate buffering agent. In some embodiments, both citric acid and potassium phosphate monobasic are present in the suppository.

The suppository may be a multi-layered single phase system where the API is stored in the core and one or more buffering agents are in an outer layer, which may rapidly disperse and/or melt. On insertion into the vaginal cavity the suppository base may melt and/or disperse, thereby releasing the buffering agent(s), which can provide protons that can be used to release NO from the API dispersed in the core.

Additional excipients that may be included in the vaginal suppository include preservatives (e.g., parabens) optionally in an amount of about 0.01% to about 1.0% by weight of the suppository, lubricants (e.g., mineral oil) optionally in an amount of about 1% to about 10% by weight of the suppository, and/or hard waxes optionally in an amount of about 1 to about 10% by weight of the suppository.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A suppository comprising:
    a nitric oxide-releasing active pharmaceutical ingredient,
        wherein the nitric oxide-releasing active pharmaceutical ingredient is a macromolecule that comprises a crosslinked or non-crosslinked polymer, dendrimer, metallic compound, organometallic compound, or inorganic-based compound, wherein the macromolecule has a molecular weight of 500 Daltons or greater;
    a suppository base; and
    a proton source;
    wherein the nitric oxide-releasing active pharmaceutical ingredient is within the suppository base, and
    wherein the suppository releases nitric oxide in an amount of about 0.01% to about 10% by weight of the suppository, as measured by real time in vitro release testing.

2. The suppository of claim 1, wherein the nitric oxide-releasing active pharmaceutical ingredient is present in an amount of about 0.1% to about 70% by weight of the suppository.

3. The suppository of claim 1, wherein the suppository base is present in an amount of about 0.01% to about 99.91% by weight of the suppository.

4. The suppository of claim 1, wherein the suppository base comprises *theobroma* oil, triglyceride, monoglyceride and diglyceride esters of $C_8$-$C_{20}$ fatty acids and the mixtures thereof, gelatin, polyethylene glycol (PEG), and/or glycerolated glycerin, and
    wherein the fatty acids comprise capric acid, caprylic acid, eicosenoic acid, stearic acid, lauric acid, myristic acid, oleic acid, palmitic acid, ricinoleic acid and their derivatives.

5. The suppository of claim 1, wherein the suppository base is hydrophobic or hydrophilic.

6. The suppository of claim 1, wherein the suppository further comprises a buffering agent in an amount of about 0.1% to about 30% by weight of the suppository.

7. The suppository of claim 1, wherein the suppository further comprises at least two buffering agents, and
    wherein each of the at least two buffering agents is present in an amount of about 0.1% to about 30% by weight of the suppository.

8. The suppository of claim 6, wherein the buffering agent is selected from the group consisting of potassium phosphate monobasic, phosphoric acid, citric acid, acetic acid, lactic acid, boric acid, succinic acid, malic acid, sodium citrate dihydrate, and any combination thereof.

9. The suppository of claim 1, wherein the suppository further comprises a preservative in an amount of about 0.1% to about 2% by weight of the suppository.

10. The suppository of claim 1, wherein the suppository further comprises a solvent in an amount of about 0.1% to about 99% by weight of the suppository.

11. The suppository of claim 10, wherein the solvent is selected from the group consisting of acetone, methyl alcohol, ethanol, isopropanol, butyl alcohol, ethyl acetate, dimethyl isosorbide, propylene glycol, glycerin, ethylene glycol, polyethylene glycol, diethylene glycol monoethyl ether, water, and any combination thereof.

12. The suppository of claim 1, wherein the suppository further comprises a lubricant in an amount of about 1% to about 10% by weight of the suppository.

13. The suppository of claim 12, wherein the lubricant is selected from the group consisting of magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, mineral oil, and any combination thereof.

14. The suppository of claim 1, wherein the suppository further comprises mineral oil in an amount of about 1% to about 20% by weight of the suppository.

15. The suppository of claim 1, wherein the suppository further comprises one or more hard waxes in an amount of about 1% to about 20% by weight of the suppository.

16. The suppository of claim 1, wherein the nitric oxide-releasing active pharmaceutical ingredient comprises a co-condensed silica network comprising diazeniumdiolated methylaminopropyl trimethoxysilane (MAP3) and tetraethyl orthosilicate (TEOS).

17. The suppository of claim 1, wherein the suppository administers nitric oxide in an amount sufficient to induce apoptosis in virally infected cells.

18. The suppository of claim 1, wherein the suppository administers nitric oxide in an amount sufficient to reduce or eliminate viral replication with less than about 50% host cell cytotoxicity.

19. The suppository of claim 1, wherein the suppository is a vaginal suppository.

20. The suppository of claim 1, wherein the suppository is a single phase system.

21. A suppository comprising:
a nitric oxide-releasing active pharmaceutical ingredient, wherein the nitric oxide-releasing active pharmaceutical ingredient is a macromolecule that comprises a crosslinked or non-crosslinked polymer, dendrimer, metallic compound, organometallic compound, or inorganic-based compound, wherein the macromolecule has a molecular weight of 500 Daltons or greater;
a suppository base; and
a buffering agent in an amount of about 0.1% to about 30% by weight of the suppository;
wherein the nitric oxide-releasing active pharmaceutical ingredient is within the suppository base, and
wherein the suppository releases nitric oxide in an amount of about 0.01% to about 10% by weight of the suppository, as measured by real time in vitro release testing.

22. The suppository of claim 21, wherein the buffering agent is selected from the group consisting of potassium phosphate monobasic, phosphoric acid, citric acid, acetic acid, lactic acid, boric acid, succinic acid, malic acid, sodium citrate dihydrate, and any combination thereof.

23. The suppository of claim 21, wherein the nitric oxide-releasing active pharmaceutical ingredient comprises a co-condensed silica network comprising diazeniumdiolated methylaminopropyl trimethoxysilane (MAP3) and tetraethyl orthosilicate (TEOS).

24. The suppository of claim 21, wherein the suppository is a vaginal suppository.

* * * * *